(12) United States Patent
Laurence et al.

(10) Patent No.: US 8,475,476 B2
(45) Date of Patent: Jul. 2, 2013

(54) SYSTEM AND METHOD FOR ACCESSING A BODY CAVITY

(75) Inventors: Bernard H. Laurence, Fremantle (AU); David F. Waller, Winston-Salem, NC (US); David M. Hardin, Winson-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 348 days.

(21) Appl. No.: 11/141,449

(22) Filed: May 31, 2005

(65) Prior Publication Data

US 2006/0015006 A1   Jan. 19, 2006

Related U.S. Application Data

(60) Provisional application No. 60/575,958, filed on Jun. 1, 2004, provisional application No. 60/648,791, filed on Feb. 1, 2005.

(51) Int. Cl.
*A61B 17/04* (2006.01)

(52) U.S. Cl.
USPC .......................................... 606/148

(58) Field of Classification Search
USPC ............... 606/139, 148, 144, 145, 213, 108, 606/150, 184, 185; 600/114, 121, 120, 123, 600/125, 186
See application file for complete search history.

(56) References Cited

U.S. PATENT DOCUMENTS

| | | |
|---|---|---|
| 3,809,081 A | 5/1974 | Loveless |
| 4,807,593 A | 2/1989 | Ito |
| 5,025,778 A | 6/1991 | Silverstein et al. |
| 5,059,183 A | 10/1991 | Semrad |
| 5,112,308 A | 5/1992 | Olsen et al. |
| 5,158,543 A | 10/1992 | Lazarus |
| 5,222,508 A | 6/1993 | Contarini |
| 5,258,003 A | 11/1993 | Ciaglia et al. |
| 5,304,184 A | 4/1994 | Hathaway et al. |
| 5,320,610 A | 6/1994 | Yoon |
| 5,320,632 A | 6/1994 | Heidmueller |
| 5,350,385 A | 9/1994 | Christy |
| 5,364,408 A | 11/1994 | Gordon |
| 5,368,601 A | 11/1994 | Sauer et al. |

(Continued)

FOREIGN PATENT DOCUMENTS

WO      WO 02/11605      *   2/2002

OTHER PUBLICATIONS

Communication Pursuant to Article 94(3) EPC for EPO Application No. 05 253 370.0-2310 Mailed Jan. 21, 2009.

*Primary Examiner* — Thomas McEvoy
(74) *Attorney, Agent, or Firm* — Brinks Hofer Gilson & Lione

(57) ABSTRACT

A device and method for accessing the interior of a cavity of a patient is described. The transmural access system includes an overtube for use with an endoscope, a safety trocar, suture anchors, and a suture exchanger. The overtube is deployed in conjunction with an endoscope through a selected body passageway of a patient to locate a sight for an access portal. The distal end of the multi-lumen overtube is secured to an interior body wall of the selected access portal. A safety trocar is advanced through the main lumen of the overtube to form the access portal to the body cavity. Upon completion of the desired medical procedure, the access portal can be closed by deploying a suture exchanger.

9 Claims, 15 Drawing Sheets

U.S. PATENT DOCUMENTS

| | | | |
|---|---|---|---|
| 5,374,275 A | 12/1994 | Bradley et al. | |
| 5,391,182 A | 2/1995 | Chin | |
| 5,403,329 A | 4/1995 | Hinchcliffe | |
| 5,417,699 A | 5/1995 | Klein et al. | |
| 5,431,151 A | 7/1995 | Riek et al. | |
| 5,439,469 A | 8/1995 | Heaven et al. | |
| 5,445,142 A | 8/1995 | Hassler, Jr. | |
| 5,462,561 A | 10/1995 | Voda | |
| 5,470,338 A | 11/1995 | Whitfield et al. | |
| 5,476,469 A | 12/1995 | Hathaway et al. | |
| 5,478,353 A | 12/1995 | Yoon | |
| 5,522,833 A | 6/1996 | Stephens et al. | |
| 5,554,097 A | 9/1996 | Guy | |
| 5,562,683 A | 10/1996 | Chan | |
| 5,571,114 A | 11/1996 | Devanaboyina | |
| 5,573,540 A | 11/1996 | Yoon | |
| 5,586,986 A | 12/1996 | Hinchliffe | |
| 5,591,190 A | 1/1997 | Yoon | |
| 5,591,191 A | 1/1997 | Kieturakis | |
| 5,626,614 A * | 5/1997 | Hart | 606/232 |
| 5,630,805 A | 5/1997 | Ternamian | |
| 5,643,292 A | 7/1997 | Hart | |
| 5,653,717 A | 8/1997 | Ko et al. | |
| 5,653,718 A | 8/1997 | Yoon | |
| 5,662,673 A | 9/1997 | Kieturakis | |
| 5,676,681 A | 10/1997 | Yoon | |
| 5,676,682 A | 10/1997 | Yoon | |
| 5,676,683 A | 10/1997 | Yoon | |
| 5,688,286 A | 11/1997 | Yoon | |
| 5,690,663 A | 11/1997 | Stephens | |
| 5,700,273 A | 12/1997 | Buelna et al. | |
| 5,707,355 A | 1/1998 | Zimmon | |
| 5,743,851 A | 4/1998 | Moll et al. | |
| 5,772,678 A | 6/1998 | Thomason et al. | |
| 5,827,319 A | 10/1998 | Carlson et al. | |
| 5,836,955 A | 11/1998 | Buelna et al. | |
| 5,836,956 A | 11/1998 | Buelna et al. | |
| 5,842,971 A | 12/1998 | Yoon | |
| 5,846,253 A | 12/1998 | Buelna et al. | |
| 5,860,990 A | 1/1999 | Nobles et al. | |
| 5,879,332 A | 3/1999 | Schwemberger | |
| 5,882,344 A * | 3/1999 | Stouder, Jr. | 604/264 |
| 5,882,345 A | 3/1999 | Yoon | |
| 5,885,217 A | 3/1999 | Gisselberg et al. | |
| 5,901,424 A | 5/1999 | Rector | |
| 5,906,595 A | 5/1999 | Powell | |
| 5,947,930 A | 9/1999 | Schwemberger | |
| 5,954,732 A * | 9/1999 | Hart et al. | 606/144 |
| 5,997,510 A | 12/1999 | Schwemberger | |
| 6,007,481 A | 12/1999 | Rick et al. | |
| 6,030,365 A * | 2/2000 | Laufer | 604/164.01 |
| 6,162,236 A | 12/2000 | Osada | |
| 6,203,554 B1 | 3/2001 | Roberts | |
| 6,210,376 B1 | 4/2001 | Grayson | |
| 6,210,377 B1 | 4/2001 | Ouchi | |
| 6,315,733 B1 | 11/2001 | Zimmon | |
| 6,325,812 B1 | 12/2001 | Dubrul et al. | |
| 6,402,770 B1 | 6/2002 | Jessen | |
| 6,451,041 B1 | 7/2002 | Moenning et al. | |
| 6,506,182 B2 | 1/2003 | Estabrook et al. | |
| 6,527,753 B2 | 3/2003 | Sekine et al. | |
| 6,535,764 B2 | 3/2003 | Imran et al. | |
| 6,551,270 B1 | 4/2003 | Bimbo et al. | |
| 6,572,629 B2 | 6/2003 | Kalloo et al. | |
| 6,616,678 B2 | 9/2003 | Nishtala et al. | |
| 6,733,479 B1 | 5/2004 | Ott | |
| 6,743,207 B2 | 6/2004 | Elbert et al. | |
| 6,849,078 B2 | 2/2005 | Durgin et al. | |
| 2001/0049497 A1 | 12/2001 | Kalloo et al. | |
| 2002/0007153 A1 | 1/2002 | Wells et al. | |
| 2002/0151921 A1* | 10/2002 | Kanner et al. | 606/190 |
| 2002/0188304 A1* | 12/2002 | Mollenauer et al. | 606/148 |
| 2002/0193806 A1 | 12/2002 | Moening et al. | |
| 2002/0198554 A1 | 12/2002 | Whitman et al. | |
| 2003/0065359 A1 | 4/2003 | Weller et al. | |
| 2003/0088212 A1 | 5/2003 | Tai | |
| 2003/0114917 A1* | 6/2003 | Holloway et al. | 623/1.13 |
| 2003/0167063 A1* | 9/2003 | Kerr | 606/144 |
| 2003/0229296 A1 | 12/2003 | Ishikawa et al. | |
| 2004/0082969 A1* | 4/2004 | Kerr | 606/205 |
| 2005/0119670 A1* | 6/2005 | Kerr | 606/144 |

* cited by examiner

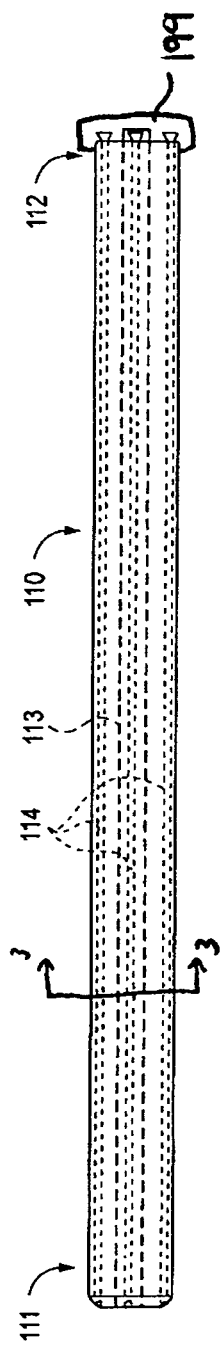
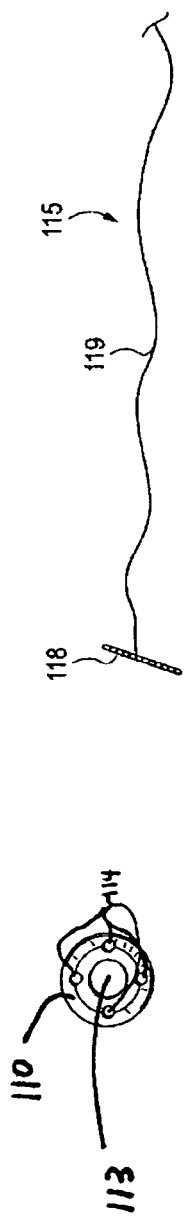
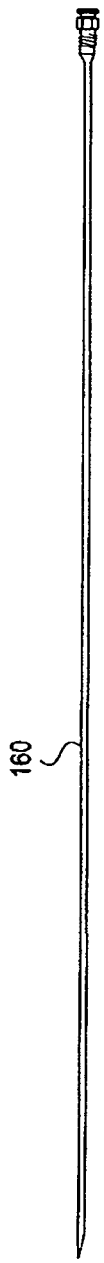
FIG. 2
FIG. 3
FIG. 4
FIG. 5

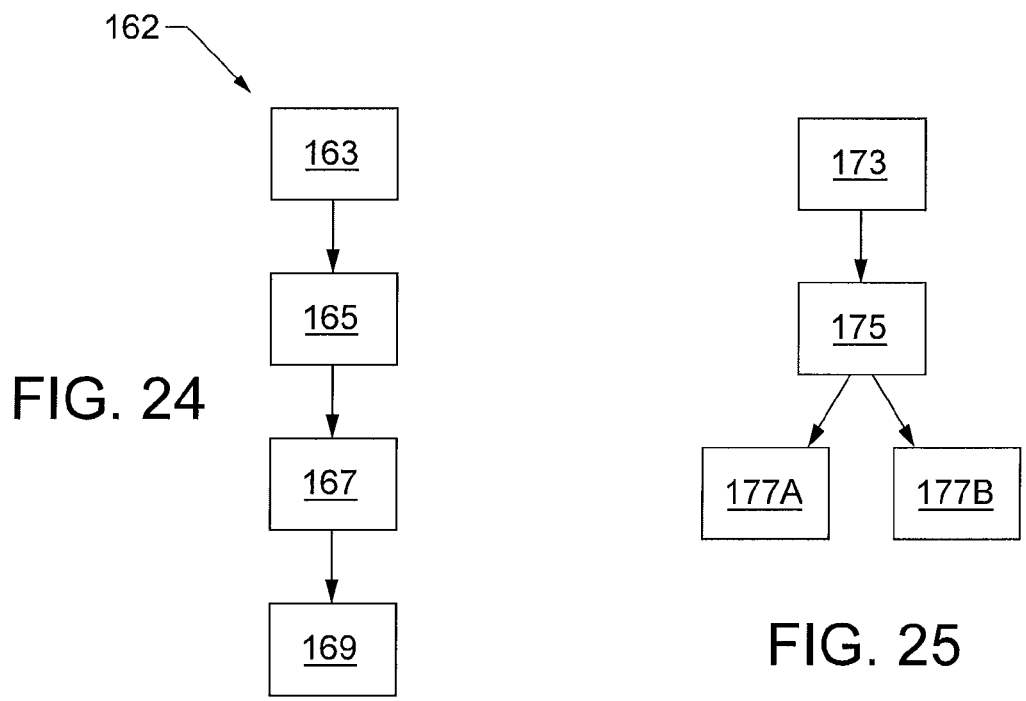
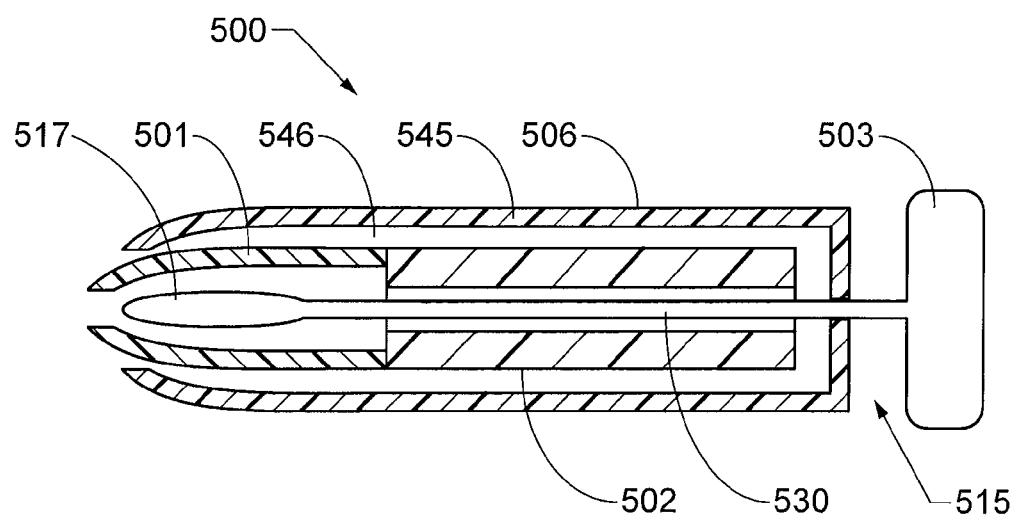

SYSTEM AND METHOD FOR ACCESSING A BODY CAVITY

RELATED APPLICATIONS

This application claims the benefit of priority from U.S. Provisional Application No. 60/575,958 filed Jun. 1, 2004 and U.S. Provisional Application No. 60/648,791, filed Feb. 1, 2005, which are incorporated herein by reference.

TECHNICAL FIELD

The invention generally relates to methods and devices for accessing a body cavity of a patient.

BACKGROUND

For some time, open surgery has been used to access a body cavity of a patient to examine or treat various diseases or injuries. Open surgery typically involves forming a transabdominal incision through the abdomen wall. This incision provides a physician with direct access to the peritoneal cavity and its organs. As generally illustrated in FIG. 1, the peritoneum 1 includes a main cavity or greater sac 2, which contains the small intestine 6, transverse colon 7, stomach 8, liver 9, bare area of liver 10, pancreas 11, duodenum 12, aorta 13, and mesentery 14.

An alternative and somewhat less traumatic surgical technique used to access an internal cavity of a patient involves laparoscopy. During laparoscopy, a laparoscope and other surgical instruments are inserted through one or more small incisions of the anterior abdominal wall, e.g., a transumbilical incision. Patients undergoing laparoscopy generally have shorter recovery times and less incision pain than those using traditional open surgery.

However, open and laparascopic surgery have numerous drawbacks. In the case of open surgery those drawbacks include relatively long and painful recovery periods, a heightened risk of infection, and large, aesthetically undesirable scars. In the case of laparascopic procedures, there are other drawbacks. For example, laparascopic techniques may be unsuitable for some patients, including pregnant women, and those with previous abdominal surgery. And, although not as severe as in open surgery, patients are left with aesthetically undesirable scars where incisions are made to access the abdomen.

SUMMARY

Accordingly, it is an object of the present invention to provide a medical device, system, and method that resolves or improves upon one or more of the above-described drawbacks.

In one aspect, the foregoing object is obtained by providing access to a body cavity, such as the peritoneal cavity, via the stomach or rectum. This is accomplished by a transmural access system. The transmural access system includes an overtube that is flexible and has a plurality of lumens. One of the lumens is configured to receive an endoscope. Additional lumens can be provided to pass an attachment mechanism, such as suture anchors, to the distal end of the overtube.

In a second aspect, the transmural access system includes a trocar and sheath for forming and maintaining an access portal in a body wall. The trocar is configured to pass through one of the lumens of the overtube. The trocar and sheath preferably have an axial length between 50 cm and 100 cm. An alternative safety trocar is also disclosed. The safety trocar includes at its distal end an obturator tip. The obturator tip is slidable between a first position and a second position. In the first position the distal tip is located distally to the trocar tube distal end, and in the second position, the distal tip is located proximal to the trocar tube distal end. A dilator tip is operably connected to the distal end of the trocar tube.

In a third aspect, the transmural access system includes a suture exchanger for use with the overtube. The suture exchanger is configured to catch or secure suture anchors and withdraw the suture ends proximally through the overtube. The suture exchanger includes a shaft having a proximal end, a distal end, and a central portion therebetween. The central portion has an axial length between 30 centimeters and 120 centimeters and an outside diameter less than 3 centimeters. A hook or other tool is formed on the distal end of the shaft in order to catch or secure the sutures. The shaft can then be removed from the overtube, thereby withdrawing the distal ends of the sutures for knotting.

In a fourth aspect, a method is disclosed for transmurally accessing a body cavity of a patient. The method includes providing a multi-lumen overtube having a proximal end, a distal end, a main lumen and at least one attachment lumen. An endoscope is positioned to extend through at least a portion of the main lumen. At least one attachment mechanism is provided to extend through at least a portion of the at least one attachment lumen. The overtube can then be advanced through a body orifice into and along at least a portion of a body passageway such that the distal end is adjacent a selected portal sight along a body wall (e.g., the stomach). The distal end of the overtube is then secured to the body wall at the selected portal sight by advancing the at least one attachment mechanism through the at least one attachment lumen and into the body wall adjacent the selected portal sight. The endoscope can then be withdrawn from the main lumen, and a flexible trocar advanced therethrough. The flexible trocar is used to form a portal at the selected portal sight. Once a portal is formed, the endoscope can be readvanced through the main lumen so that a distal end of the endoscope is disposed adjacent or through the portal. This allows viewing at least a portion of the body cavity. After the desired examination or procedure is complete, the portal can be sutured by traditional techniques or with a suture anchor.

BRIEF DESCRIPTION OF THE DRAWINGS

Embodiments of the present invention will now be described by way of example with reference to the accompanying drawings, in which:

FIG. 2 is cross-sectional view of a flexible, multi-lumen overtube according to an embodiment of the present invention;

FIG. 3 is a sectional view of the overtube of FIG. 2 taken along line 3-3;

FIG. 4 is a view of a suture anchor according to an embodiment of the present invention;

FIG. 5 is a side-view of a needle introducer according to an embodiment of the present invention;

FIG. 24 is a flow-chart showing a method of using a suture exchanger;

FIG. 25 is a flow-chart showing a method of ligating a puncture site;

FIG. 26 is a cross-sectional side view showing the flexible, long safety trocar in accordance with an embodiment of the present invention;

DETAILED DESCRIPTION OF THE PREFERRED EMBODIMENTS

Figure 1:
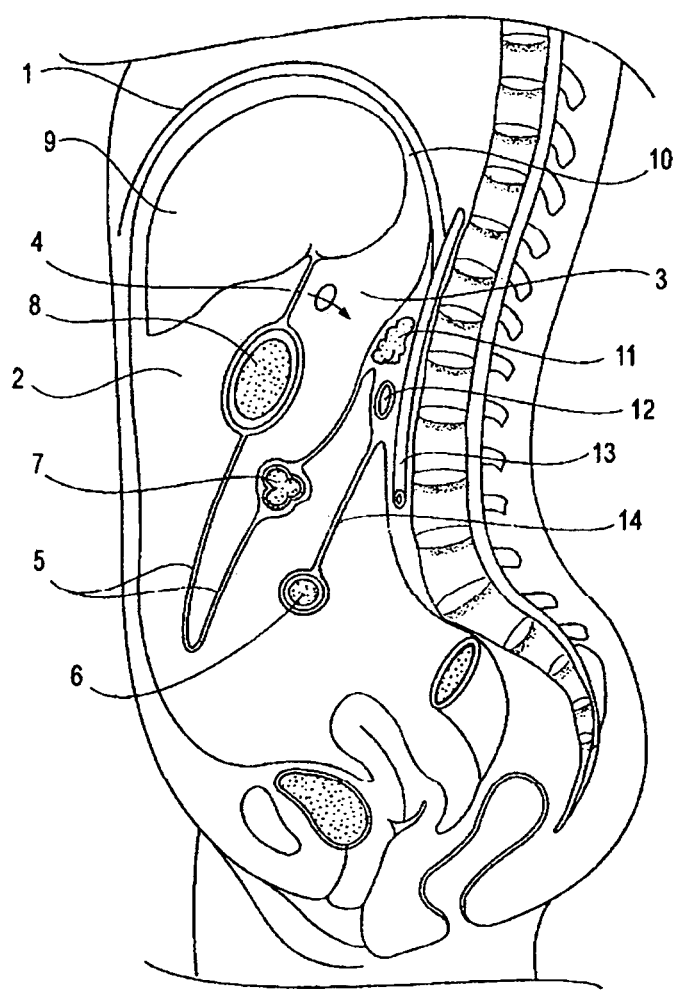
FIG. 1 is a partial, cross-sectional view of the peritoneum 1 that lines the wall the abdominal cavity and folds inwards to enclose the viscera.
Figure 6:
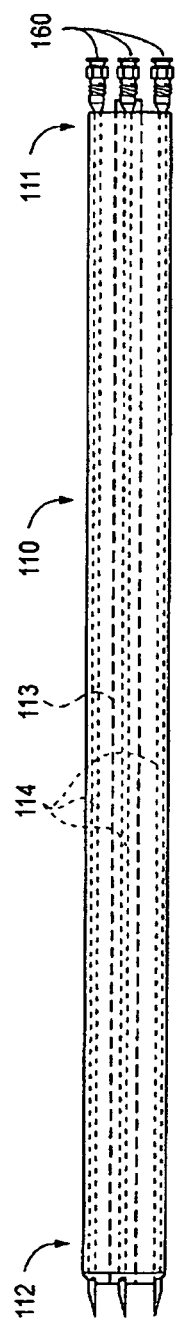
FIG. 6 is a cross-sectional view of needle introducers inserted into the overtube of FIG. 2.
Figure 7:
FIG. 7 is a side-view of a pushing rod according to an embodiment of the present invention.

Referring now to the Figures wherein like numerals indicate the same element throughout the views, there is shown in FIG. 1 an abdominal cavity of a patient. More specifically, FIG. 1 illustrates the peritoneum lining the walls of the abdominal cavity and folding inward to enclose the viscera. The peritoneum comprises a main cavity, or greater sac, 2 and the omental bursa, or lesser sac, 3, which are connected by the epiploic foramen 4. Numerous peritoneal folds extend between the various organs to hold the viscera in position.

A new paradigm to access the tissues and organs of a patient is to examine them with a flexible endoscope passed through a portal formed in a natural passageway of a patient. In one non-limiting example, such an approach is used to access the pancreas through the stomach wall. Using this approach, a flexible endoscope is passed into a patient's mouth through the esophagus, stomach, posterior stomach wall and into the lesser sac. This approach enables direct inspection of the pancreas for visual diagnosis, guided high-frequency ultra-sound with a probe, targeted biopsy, or direct access for therapy. Although the invention is described with reference to peritoneal access through the esophagus and stomach wall, one of ordinary skill in the art would appreciate the peritoneal cavity may also be accessed through other body passageways such as the colon by way of a non-limiting example. Further, application of the principles of the invention to access other body cavities, such as the thoracic cavity by way of a non-limiting example, is also within the ordinary skill in the art.

Referring now to FIGS. 2-11 and 17-23, a transmural access system made in accordance with an embodiment of the present invention is shown. In general, the transluminal access system includes a flexible, multi-lumen overtube 110, an attachment mechanism 115, a flexible trocar 130, and a suture exchanger 140. The overtube is used in combination with an endoscope to establish a passageway to a target portal site in the stomach. The attachment mechanism, which includes one or more suture anchors, is used to attach the overtube to the stomach wall. Once the overtube is attached to the stomach wall, the flexible trocar is passed through the overtube, and is used to puncture the stomach wall, thereby creating access to the peritoneal cavity. Once a desired procedure in the peritoneal cavity is complete, the suture exchanger is used to retract the suture anchors, as described in greater detail below.

The flexible, multi-lumen overtube 110 comprises a distal end 111, a proximal end 112, a main lumen 113 and at least one attachment lumen 114. Any arrangement of the main lumen and the at least one attachment lumen is contemplated. FIGS. 2 and 3 illustrate one embodiment of the flexible, multi-lumen overtube having a main lumen 113 with four attachment lumens 114 equally spaced about the main lumen 113. The flexible multi-lumen overtube 110 can have a single-piece construction as shown in the embodiment depicted in FIGS. 2 and 3. Alternatively, several tubes may be bonded together to form the flexible, multi-lumen overtube 110. The flexible, multi-lumen overtube 110 can be made from any suitable material known in the art including, but not limited to, polyethylene ether ketone (PEEK), polytetrafluorethylene (PTFE), polyamide, polyurethane, polyethylene and nylon, including multi-layer or single layer structures and may also include reinforcement wires, braid wires, coils and or filaments. Optionally, the flexible, multi-lumen overtube 110 further comprises valve 199 over its proximal end 112. Valve 199 forms a seal between the flexible, multi-lumen overtube 110 and the endoscope or other device that is advanced therethrough to prevent the loss of any pressurized fluid that is introduced through the endoscope or other device, as will be explained in further detail below. In one embodiment, valve 199 is removable. One of ordinary skill in the art would know how to assemble valve 199 over the proximal end 112 of multi-lumen overtube 110.

Figure 14:
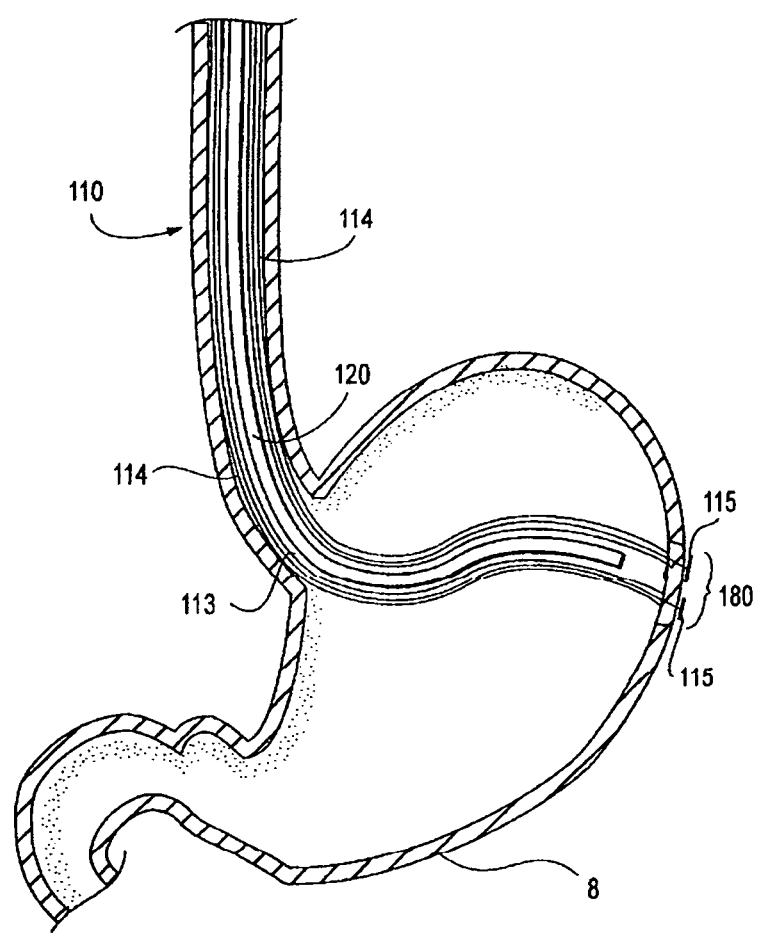
FIG. 14 is a partial, cross-sectional view illustrating the overtube distal end secured to the selected portal sight of the stomach wall with suture anchors and an endoscope positioned within the overtube.
Figure 15:
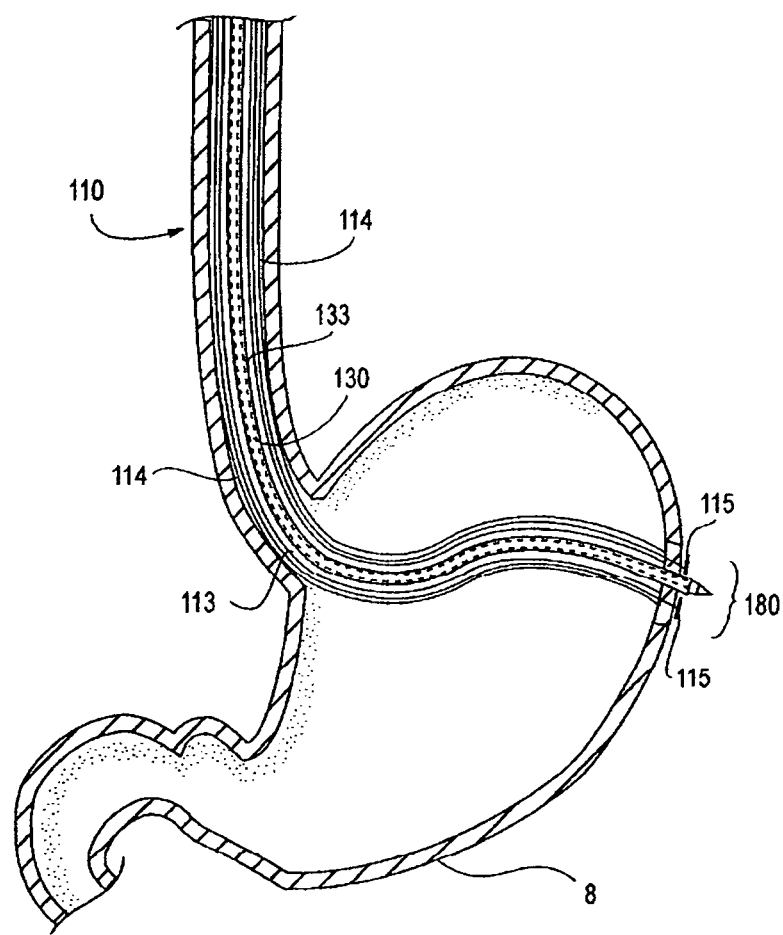
FIG. 15 is a partial, cross-sectional view showing the overtube distal end secured to the selected portal sight of the stomach wall with suture anchors and a sheathed flexible trocar puncturing the selected portal sight such that the sheath and the flexible trocar extend through the stomach wall.
Figure 18:
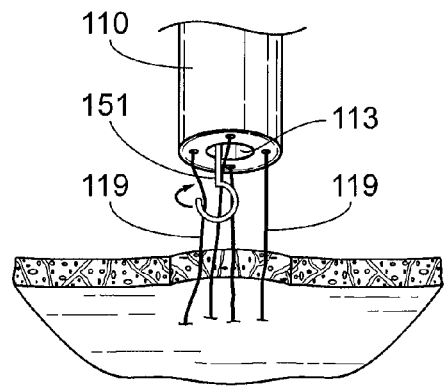
FIG. 18 is a perspective side view showing the overtube distal end, suture anchors extending from the stomach wall into the attachment lumens of the overtube, and an exemplary suture exchanger engaging the suture anchors.
Figure 19:
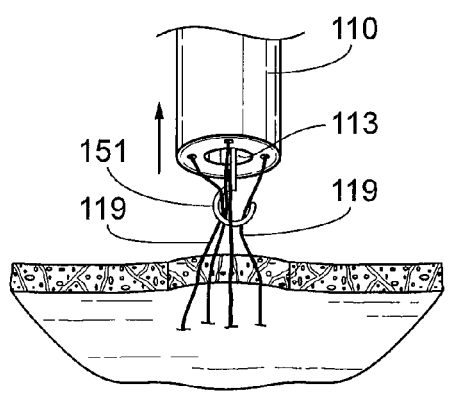
FIG. 19 is a perspective side view showing the overtube distal end, suture anchors extending from the stomach wall into the attachment lumens of the overtube, and an exemplary suture exchanger retracting the suture anchors.
Figure 20:
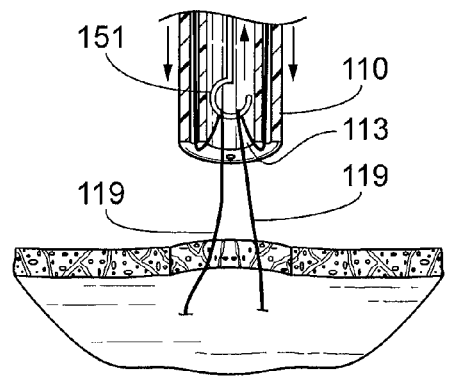
FIG. 20 is a cross-sectional side view showing the exemplary suture exchanger withdrawing the suture anchors through the central lumen of the overtube.

The main lumen 113 is configured to receive and pass an endoscope 120, as shown in FIG. 14, a flexible trocar 130, as shown in FIG. 15, or an exchanger 151, as shown in FIGS. 18-20. The main lumen 113 ranges in size from about 4 mm to about 9 mm. These sizes are provided for illustrative purposes only and are not intended to be construed as a limitation of the present invention. As one of ordinary skill in the art would appreciate, since the endoscope 120 and the flexible trocar 130 are advanced through the main lumen 113, the size of the main lumen 113 is related to the size of either the endoscope 120 or the flexible trocar 130, which ever is larger. One of ordinary skill in the art would also appreciate that the size of the trocar is related to the size of the medical instruments that are passed therethrough for the diagnosis and treatment of the tissues and organs within the body cavity. Thus, a flexible, multi-lumen overtube having a main lumen smaller than about 4 mm used with endoscopes or trocars having an outer diameter smaller than about 4 mm that may become available in the future are contemplated as being within the scope of the claims of the present invention.

The attachment lumen 114 is configured to receive and pass an attachment mechanism 115 (see FIG. 4). In one embodiment of the flexible, multi-lumen overtube 110, the at least one attachment lumen 114 and the main lumen 113 comprise a longitudinal slit (not shown) along its length so that the attachment mechanism 115 can be pulled from the at least one attachment lumen 114 into the main lumen 113 as explained more fully below.

With respect to the attachment mechanism 115 of the transmural access system of the present invention, any mechanism configured to be advanced through the attachment lumen, secure the overtube distal end 111 to a body wall, and ligate a portal in the body wall is contemplated. FIG. 4 illustrates a non-limiting embodiment of an attachment mechanism comprising a suture anchor 115. One exemplary suture anchor 115 comprises a spring coil anchor 118 and a suture portion 119, such as the Cope suture anchor manufactured by Cook, Incorporated, Bloomington, Ind.

Figure 21:
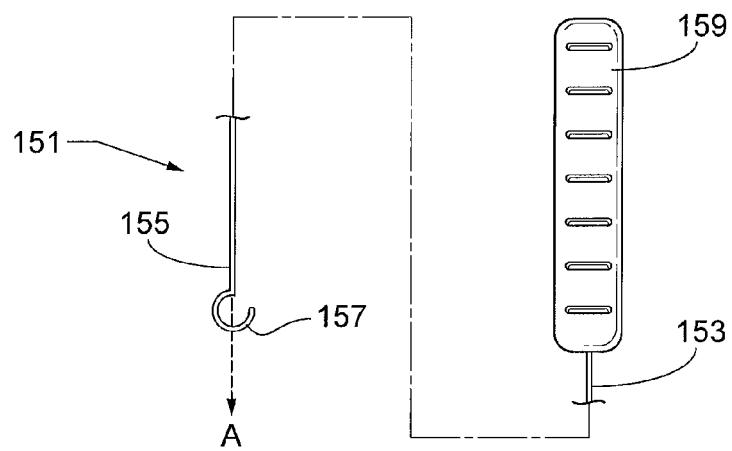
FIG. 21 is a perspective side view of a retroactor for use with the overtube.

As illustrated in FIG. 21, the suture exchanger 151 generally comprises a shaft having proximal portion 153 and distal portion 155. The suture exchanger is sized to fit through the main lumen of the overtube 110. The suture exchanger will generally have a length between 50 cm and 100 cm. However, a suture exchanger having a shorter length, for example for pediatric applications, could alternatively be used. The suture exchanger can be formed from any number of materials that can impart axial rotation from the proximal portion to the distal portion of the shaft, while maintaining the flexibility necessary to pass through the central passageway of the overtube. For example, suture exchanger can be formed from stainless steel, a rigid plastic, or a superelastic allow such as nickel-titanium.

As illustrated in FIG. 21, proximal portion 153 of suture exchanger 151 includes a handle 159 that allows a physician to easily grip and control the suture exchanger. The distal portion 153 of suture exchanger 151 is adapted to catch, pull, loop, or ensnare the suture portion of the suture anchor(s) and then withdraw the suture portions through the main lumen, as described in greater detail below. In one embodiment, the distal portion 155 includes sickle-shaped hook 157 that is offset from the longitudinal axis A formed by the shaft. Of course, other alternatively-shaped distal portions will become apparent to one of ordinary skill in the art in view of the present disclosure.

Figure 13:
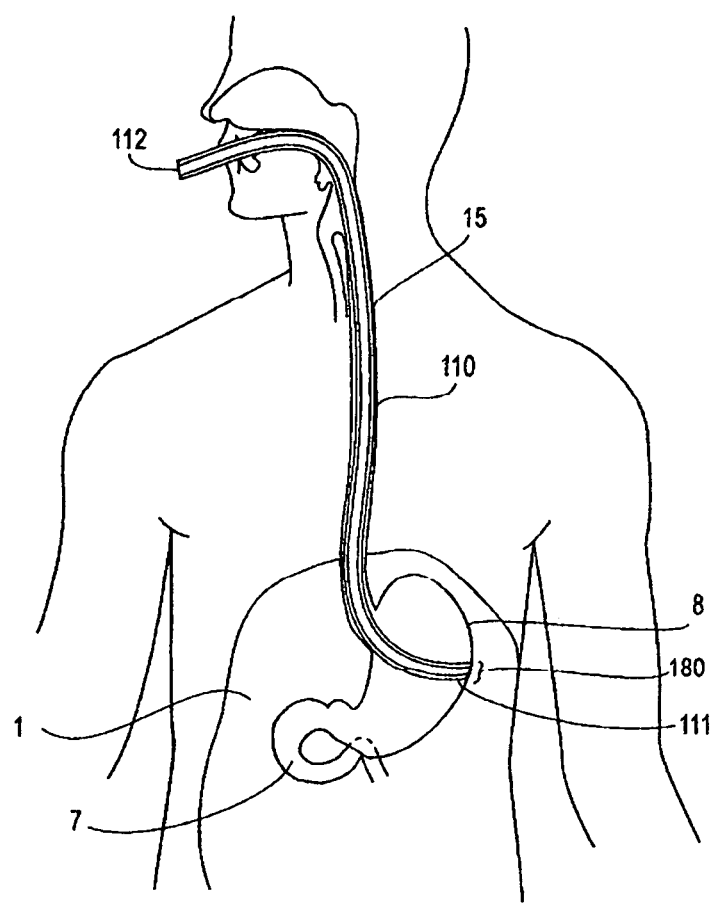
FIG. 13 is a partial, cross-sectional view showing the flexible, multi-lumen overtube of FIG. 2 positioned in the mouth and along the esophagus of a patient such that the overtube distal end is positioned against a selected portal sight of the stomach wall.

The transmural access system of the present invention is used to examine or treat tissues or organs within a body cavity, e.g. the peritoneal cavity, as follows. An endoscope 120 is disposed within the main lumen 113 of the flexible, multi-lumen overtube 110 (see FIG. 14). The flexible, multi-lumen overtube and endoscope are inserted within a body orifice of a patient. Any body orifice is contemplated including, but not limited to, the mouth or anus. The flexible, multi-lumen overtube and endoscope are advanced through a body passageway and a sight for an access portal along a body wall is selected endoscopically. For example, if access to the peritoneal cavity is sought through the mouth, esophagus and stomach, a sight for the gastric portal through the posterior stomach wall is selected as shown in FIG. 13. Alternatively, if access to the peritoneal cavity is sought through the anus, rectum and colon, a sight for an access portal through an intestinal wall is selected.

Next, the body cavity is insufflated to provide an unobstructed view of the tissues and organs therein, to protect the tissues and organs from damage as the access portal is formed and to provide a working space within the cavity. With respect to accessing the peritoneal cavity, for example, an insufflation needle (not shown) is deployed through the endoscope and punctures the stomach wall. A suitable gas, such as carbon dioxide, is injected through the endoscope to expand the peritoneal cavity. Valve 199 at the overtube proximal end prevents the gas from escaping about the endoscope.

Optionally, a wire guide is placed through the insufflation needle to maintain access to the puncture site.

After insufflation of the body cavity, the insufflation needle is removed and the overtube distal end 111 is secured to the stomach wall. In one embodiment, shown in FIGS. 24 and 14-16, at least one suture anchor 115 is passed through the at least one attachment lumen 114 and deployed into the selected portal site of the body wall 180.

Figure 8:
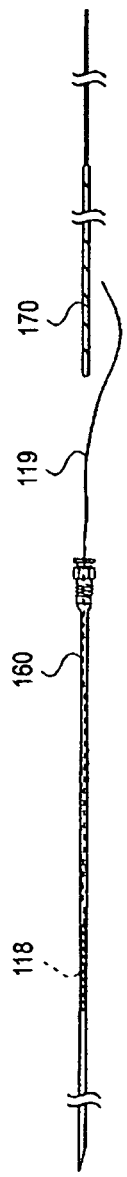
FIG. 8 is a side-view showing the suture anchor pre-loaded within the needle introducer and the pushing rod ready to be introduced into the needle introducer.
Figure 9:
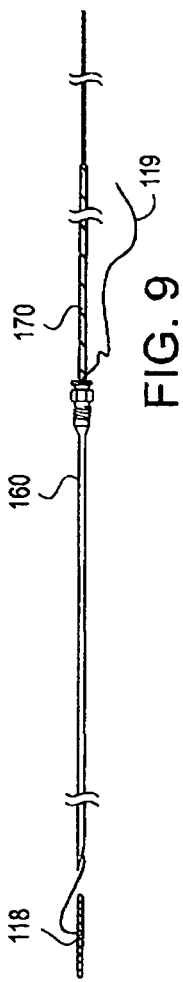
FIG. 9 is a side-view showing the pushing rod being advanced into the needle introducer and the suture anchor projecting through the needle introducer.

FIGS. 4-8 illustrate a non-limiting, exemplary method preloading and deploying the suture anchor 115 through the attachment lumen 114 of the flexible, multi-lumen overtube 110. A suture anchor 115 (shown in FIG. 4) is inserted into a needle introducer 160 (shown in FIG. 5). Once the suture anchor 115 is pre-loaded into the needle introducer 160, the needle introducer 160 is passed through the attachment lumen 114 of the flexible, multi-lumen overtube 110 (shown in FIG. 6) and the suture needle 160 is inserted through the stomach wall at the selected access portal sight. To deploy the suture anchor 115 through the attachment lumen 114, a pusher rod 170 (FIG. 7) is used to push the suture anchor 115 so that the spring coil 118 is advanced through the needle lumen 160 as shown in FIGS. 8 and 9. Once the suture anchor 115 is deployed, the needle introducer 160 is removed from the attachment lumen 114.

The overtube distal end 111 can be positioned firmly against the body wall by proximally pulling the suture portion 119 of the suture anchor 115. The proximal end suture portion 119 can be held by the physician or secured to the proximal end 112 of the flexible, multi-lumen overtube 110.

As shown in FIG. 14, since the endoscope 120 remains within the main lumen 113 of the flexible, multi-lumen overtube 110, a physician can view the deployment of the suture anchor 115 through the body wall at the selected access portal sight 180. This affords the physician the ability to attach the overtube distal end 111 against a body wall such that the main lumen 113 is precisely aligned with the selected access portal sight 180.

Once the distal end 111 of the flexible, multi-lumen overtube 110 is secured to the selected portal sight 180, the endoscope 120 is removed and a trocar 130 is advanced through the main lumen 113 of the flexible, multi-lumen overtube 110 and into the body wall to form the access portal to the body cavity as shown in FIG. 15 and as described above. If a wire guide has been placed and the trocar 130 comprises a wire guide lumen 137, then the trocar 130 is advanced over the wire guide.

Since the suture anchor 115 retains the overtube distal end 111 against the body wall at the selected portal sight 180, the overtube distal end 111 cannot shift as the physician forms the access portal through the body wall. This facilitates the formation of the access portal by providing a controlled puncture of the body wall and enables the physician to accurately locate the access portal at the selected portal sight 180. Moreover, since the overtube distal end 111 is secured against the interior body wall at the selected portal sight 180, the flexible, multi-lumen overtube 110 cannot extend or pass through the access portal. This eliminates any potential damage caused to tissues and organs within the body cavity due to over insertion of the flexible, multi-lumen overtube.

Figure 16:
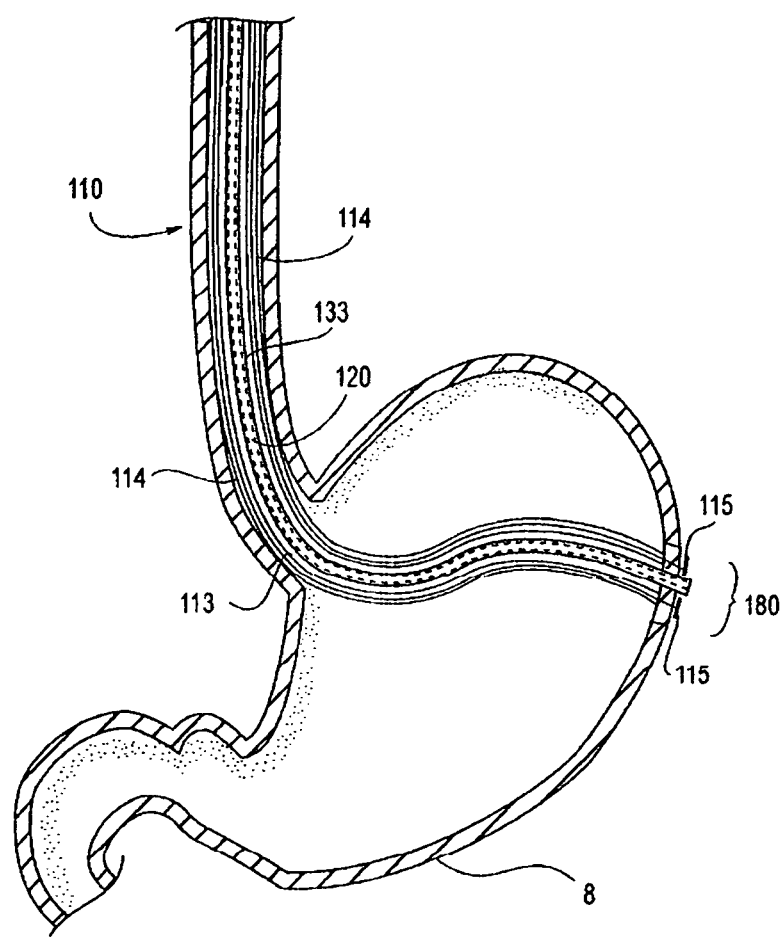
FIG. 16 is a view similar to FIG. 15 showing the flexible trocar withdrawn from the sheath, the sheath remaining extended through the stomach wall and having an endoscope disposed therein.

Once the access portal to the body cavity is formed, the trocar 130 is withdrawn. An endoscope or other instrumentation can be inserted through the main lumen 113 of the flexible, multi-lumen overtube 110 for examination, diagnosis and/or treatment of the tissues or organs within the body cavity. Alternatively, if the trocar 130 comprises an outer sheath 133 (see FIG. 15), the obturator portion of the trocar 130 can be withdrawn leaving the sheath 133 positioned through the access portal. An endoscope or other instrumentation can be inserted through the sheath 133 as shown in FIG. 16. In this embodiment, the remaining sheath forms a lumen from exterior of the patient to the body cavity. Sheath 133 further provides the advantage of protecting the tissue surrounding the access portal from trauma as an endoscope or other instrumentation is advanced therethrough to perform procedures within the body cavity. The sheath 133 also eliminates the need to dilate the access portal, which could damage the tissue surrounding the access portal to the body cavity.

Figure 17:
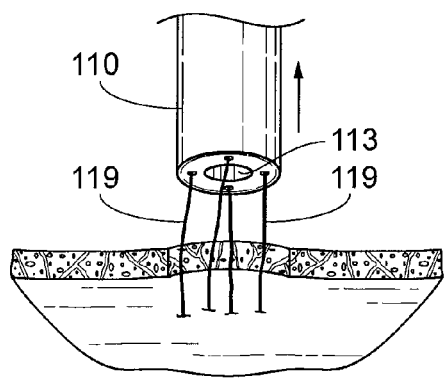
FIG. 17 is a perspective side view showing the overtube distal end partly separated from the stomach wall with suture anchors extending from the stomach wall into the attachment lumens of the overtube.

Upon completion of the desired examination and/or treatment with the body cavity, the access portal is closed by ligating the suture portions 119 of the suture anchors 115. One method of ligating the sutures is by ensnaring (FIG. 18) and withdrawing (FIGS. 19-20) the sutures through the main lumen of the overtube by using suture exchanger 151. More specifically, the sutures are unknotted or cut from the proximal end of overtube 110. As illustrated in FIG. 17, overtube 110 is then partly withdrawn from the patient, thereby exposing suture portion 119 at the distal end of overtube 110. Hook 157 of suture exchanger 151 can then ensare (FIG. 18) and withdraw (FIGS. 19-20) suture portions 119 through main lumen 113. After the sutures are extracted through the main lumen, the physician can use conventional techniques to close the trocar puncture.

FIG. 24 further illustrates this method of using suture exchanger 151. In step 163, the suture exchanger is passed through the main lumen of the overtube. In step 165, the sutures are released from the proximal end of the overtube. In step 167, the overtube is partly retracted and the suture exchanger hook is used to ensnare and withdraw the suture portions through the main lumen. In step 169, the physician ligates the sutures, thus closing the trocar puncture.

Figure 22:
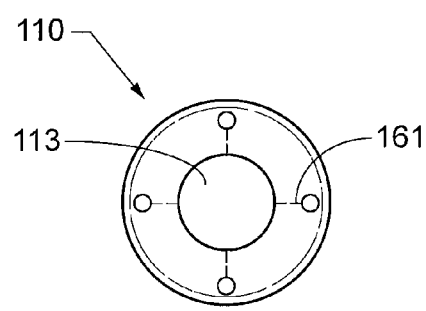
FIG. 22 is a cross-sectional view showing the overtube.
Figure 23:
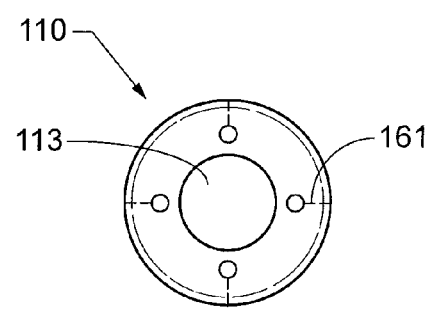
FIG. 23 is a cross-sectional view showing the overtube.

In an alternative ligating method, the suture portions of the suture anchors are pulled through a longitudinal slit 161 that extends along the length of attachment lumens 114. Longitudinal slit 161 extends from the attachment lumens into main lumen 113, as illustrated in FIG. 22, or alternatively, to the exterior of the overtube, as illustrated in FIG. 23. Instead of using a longitudinal slit, a splittable wall can be provided in the overtube. In either case, the suture portions are dislocated from the attachment lumens into either the main lumen 113 or the exterior of overtube 110. This allows the physician to tie the suture portions and ligate the trocar puncture site with the suture portions of the suture anchors. Ligation can be accomplished with conventional ligating techniques, or as described below in greater detail.

In another alternative ligating method illustrated in FIG. 25, the overtube is entirely withdrawn from the patient before the trocar puncture is ligated. In particular, as described above, upon completion of the desired examination and/or treatment with the body cavity, the sheath is removed. In step 173 of FIG. 25, the proximal ends of the suture portions are released from the overtube, thus detaching the overtube from the stomach wall. In step 175 the overtube is withdrawn from the patient, thereby leaving the proximal ends of the suture portions extending from the patient's mouth. In step 177A, the physician uses and endoscope and a flexible endoscopic suturing device to approximate the tissue surrounding the puncture site. The physician can use a flexible Sew-Right® device, which is available from Wilson-Cook Medical, Winston-Salem, N.C. Alternatively, in step 177B the physician can endoscopically trim and ligate the suture portions with conventional ligating techniques.

Figure 10:
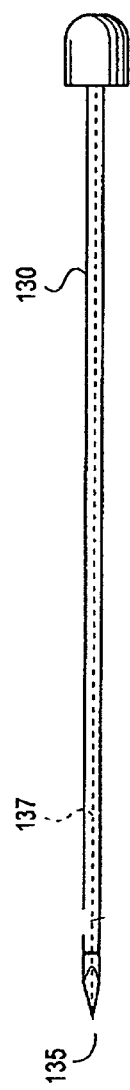
FIG. 10 is a side-view of a flexible trocar according to an embodiment of the present invention.
Figure 11:
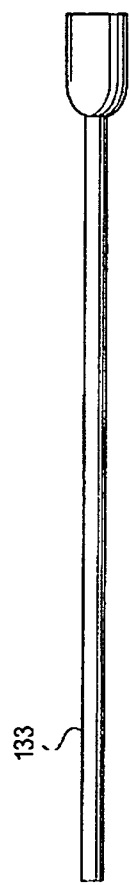
FIG. 11 is a side-view of a sheath according to an embodiment of the present invention.
Figure 12:
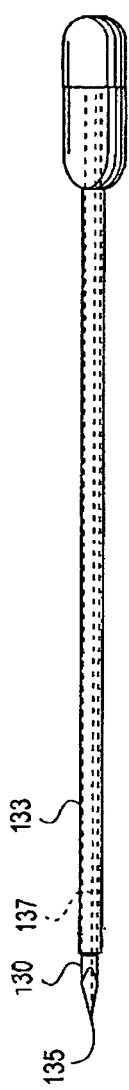
FIG. 12 is a side-view of the flexible trocar of FIG. 9 positioned within the sheath of FIG. 11.

As illustrated in FIG. 10, the flexible trocar 130 comprises an obturator having a sharp, wedge tip 135. In one embodiment, the sharp, wedge tip 135 comprises beveled edges. Optionally, the flexible trocar 130 includes a sheath 133 (see FIG. 11). Optionally, the flexible trocar further includes a wire guide lumen 137 to accommodate a wire guide (not shown) that enables a guided puncture of the body wall.

FIG. 26 illustrates an alternative safety trocar, and in particular, safety trocar 500. Safety trocar 500 includes a trocar tube 502 and obturator 515 inserted in trocar tube 502. Trocar tube 502 comprises dilator tip 501 located at the distal end of trocar tube 502 and protective outer sheath 506 disposed along an outer surface of trocar tube 502. Trocar tube 502 and dilator tip 501 can be formed from any suitable polymers known in the art, such as biocompatible polymers. Trocar tube 502 can also be provided with a PTFE coating. The coating can also comprise a hydrophilic polymer selected from the group comprising polyacrylate, copolymers comprising acrylic acid, polymethacrylate, polyacrylamide, poly(vinyl alcohol), poly(ethylene oxide), poly(ethylene imine), carboxymethylcellulose, methylcellulose, poly(acrylamide sulphonic acid), polyacrylonitrile, poly(vinyl pyrrolidoine), agar, dextran, dextrin, carrageenan, xanthan, and guar. The hydrophilic polymers can also include ionizable groups such as acid groups, e.g., carboxylic, sulphonic or nitric groups. The hydrophilic polymers may be cross-linked through a suitable cross-binding compound. The cross-binder actually-used depends on the polymer system: if the polymer system is polymerized as a free radical polymerization, a preferred cross-binder comprises 2 or 3 unsaturated double bonds.

Figure 27:
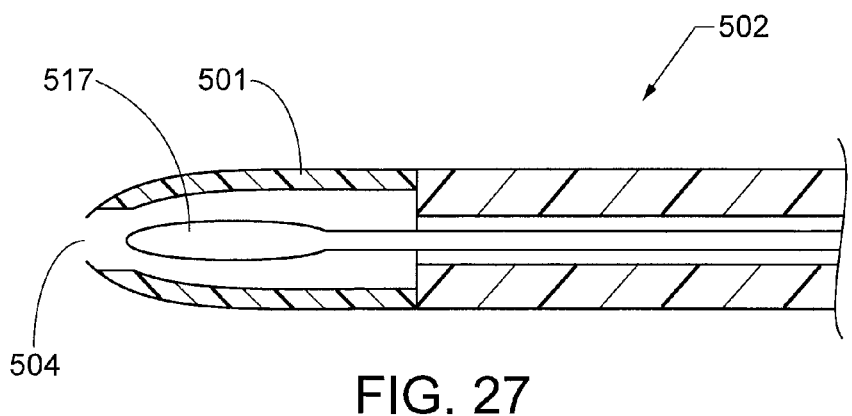
FIG. 27 is a cross-sectional side view showing the obturator tip completely retracted within the dilator tip.

Obturator 515 comprises an obturator tip 517 at the distal end of obturator 515, a handle 503 at the proximal end of obturator 515, and an elongated shaft 530 between the distal and proximal ends of obturator 515. Obturator tip 517 is biased toward a concealed position within dilator tip 501, as shown in FIGS. 26-27 and as described in greater detail below. When tissue is desired to be cut or penetrated, obturator tip 517 is extended distally through dilator tip 501 (see FIG. 36). Since obturator tip 517 is biased toward a concealed position, immediately after the desired cut is made, obturator tip 517 automatically retracts within dilator tip 501.

Figure 30:
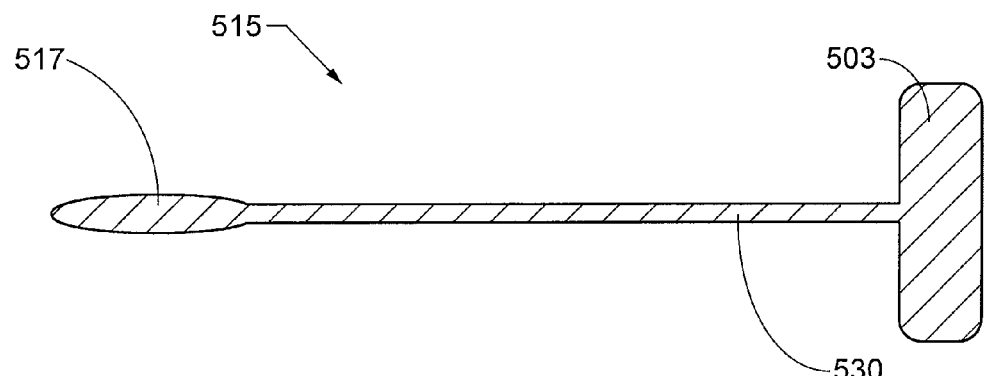
FIG. 30 is a cross-sectional side view showing the obturator for use with the safety trocar.

FIG. 30 illustrates a side view of obturator 515 having of a proximal handle 503, a distal obturator tip 517, and an elongated shaft 530 situated between the proximal and distal regions of obturator 515. Elongated shaft 530 can be manufactured from any relatively rigid, commercially available material, such as polymers or metals. Such materials should be axially strong enough to drive the obturator tip through tissue, while sufficiently flexible for endoscopic use. One such material is stainless steel, although many alternative materials will be apparent to one of ordinary skill in view of the present disclosure. As shown in FIG. 30, handle 503 is attached to the proximal end of elongated shaft 530. Handle 503 is configured to be easily grasped by a physician's hand and is preferably T-shaped. Handle 503 also provides leverage for tissue incision, puncturing, and cutting.

FIG. 27 illustrates a side view of dilator tip 501, with obturator tip 517 retracted and completely encased within dilator tip 501. Dilator tip 501 shields obturator tip 517, thereby preventing accidental or unintended puncture of tissue and internal organs while the obturator tip is not in use. Dilator tip 501 can be provided as a rounded, bullet-shaped housing that surrounds the entire outside of obturator tip 517 when obturator tip 517 is not in an extended position for cutting tissue. The surface of dilator tip 501 gradually tapers and ultimately converges at the distal end of dilator tip 501 where a longitudinal slot 504 is formed. Longitudinal slot 504 provides an orifice through which obturator tip 517 extends distally and can contact tissue.

In one embodiment, dilator tip 501 and trocar tube 502 can be constructed as an integral piece. Alternatively, dilator tip 501 can be a separately manufactured component, which is readily detached from trocar tube 502.

As FIG. 26 illustrates, protective outer sheath 506 is a separate component, axially slidable relative to trocar tube 502. Sheath 506 includes an axial passageway 546 and a lubricious exterior wall 545. The axial passageway 546 is adapted to receive trocar tube 502. There is minimal clearance between the diameter of axial passageway 546 and the diameter of trocar tube 502 in order for trocar tube 502 and obturator 515 inserted therein to be securely positioned and aligned with the desired access portal 180 to the body cavity (see FIG. 38). Surface wall 545 provides a smooth contact surface with the outer surface of trocar tube 502, thereby allowing trocar tube 502 to smoothly slide within axial passageway 546 of protective outer sheath 506.

Figure 28:
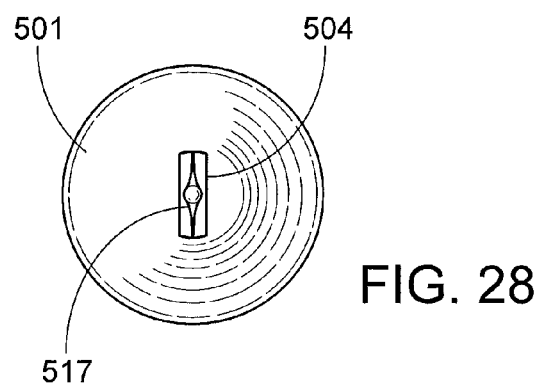
FIG. 28 is an end view of the dilator tip showing the opening through which the obturator tip extends and retracts.

FIG. 28 shows an end-view of dilator tip 501. Longitudinal slot 504 allows the obturator tip 517 to extend distally from dilator tip 501 to penetrate and cut the desired tissue and thereafter retract proximally into dilator tip 501 when the required cutting has been performed. The longitudinal slot 504 corresponds to the geometry of the obturator tip 517.

As shown in FIG. 27, the surface of dilator tip 501 is flush with trocar tube 502 outer surface so as to provide a smooth transition between trocar tube 502 and the tapered outer surface of dilator tip 501. The smooth transition ensures minimal trauma upon insertion of dilator tip 501 and trocar tube 502. Additionally, the bullet-nose shape of dilator tip 501 can be used to further dilate the tissue after obturator tip 517 has made an initial incision. Morever, dilator tip 501 is relatively wide, and thus provides a stable support or platform on which to cut tissue.

Figure 29:
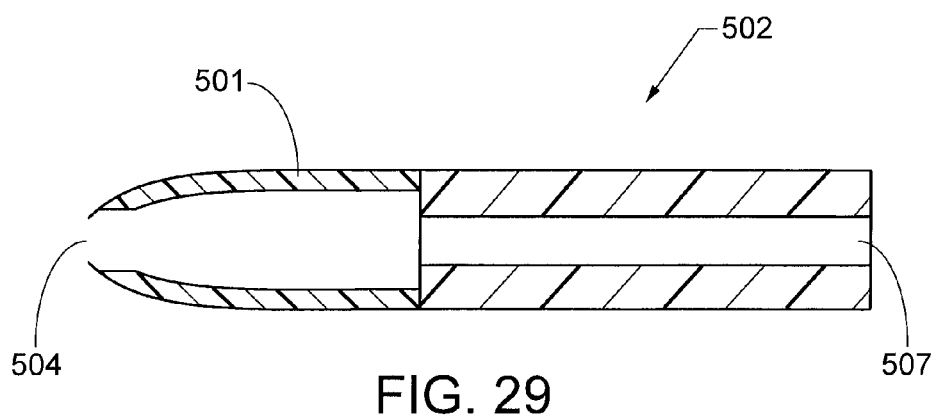
FIG. 29 is cross-sectional side view of the safety trocar without the obturator inserted.

FIG. 29 shows trocar tube 502 without obturator 515 inserted. Trocar tube 502 contains a lumen 507 through which obturator 515 is inserted and advanced therethrough until obturator tip 517 is completely encased within dilator tip 501. Clearance is preferably provided between the inside diameter of lumen 507 (FIG. 29) and the outside diameter of elongated shaft 530 of obturator 515 (FIG. 30). As a result, obturator 515 slides smoothly within trocar tube 502 during both extension and retraction of obturator tip 517.

Figure 31:
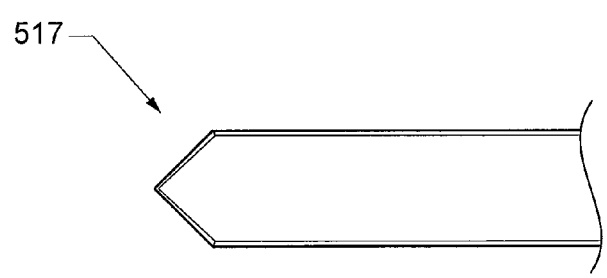
FIG. 31 is a perspective side view showing an exemplary knife edge.
Figure 32:
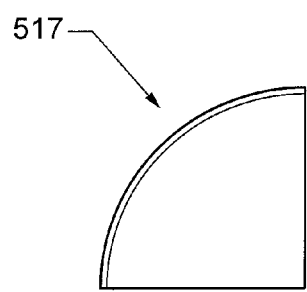
FIG. 32 is a perspective side view showing an exemplary knife edge.
Figure 33:
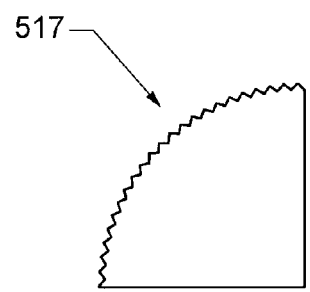
FIG. 33 is a perspective side view showing an exemplary knife edge.

Obturator tip 517 can consist of a variety of cutting edges, as shown in FIGS. 31-33. FIG. 31 shows a double-edged obturator tip 517. In an alternative embodiment shown in FIG. 32, tip 517 can be a flat, scalpel-like blade which allows for a clean incision, thereby minimizing tearing of surrounding tissue. As shown in FIG. 33, obturator tip 517 can also consist of a serrated knife edge. The serrated knife edge produces greater surface area contact with the tissue which reduces the force required to cut the tissue. Obturator tip 517 can be formed from any malleable material that can be sharpened. Examples of such materials include, but are not limited to, stainless steel and ceramics. Many alternative materials will be apparent to one of ordinary skill in view of the present disclosure.

Figure 38:
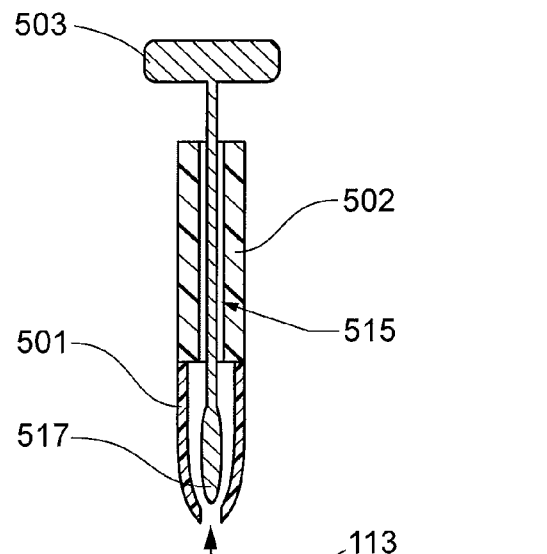
FIG. 38 is a cross-sectional view of the safety trocar tube with the obturator withdrawn and the overlying outer protective sheath positioned within an overtube according to an embodiment of the present invention.

Referring to FIG. 38, after obturator 515 and trocar tube 502 are inserted into the main lumen 113 of overtube 110, obturator tip 517 is ready to be activated to extend distally and penetrate the desired body tissue. Activating obturator tip 517 to extend through longitudinal slot 504 (FIG. 28) of dilator tip 501 can be achieved in numerous ways. FIG. 26 shows a manual safety trocar 500, in which obturator tip 517 extends distally through longitudinal slot 504 of dilator tip 501 when manual force is applied at proximal handle 503. In such an embodiment, the force applied at proximal handle 503 is transmitted to elongated shaft 530 and, ultimately, to obturator tip 517.

Figure 34:
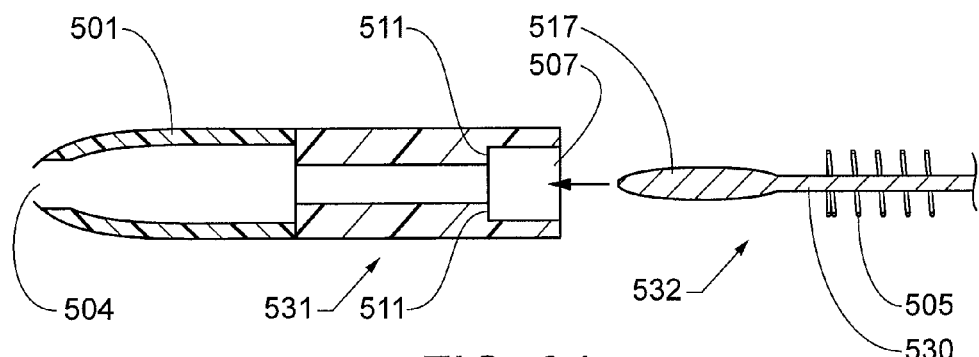
FIG. 34 is a cross-sectional side view of a trocar tube having proximal flanges and a spring-loaded obturator according to an embodiment of the present invention.
Figure 35:
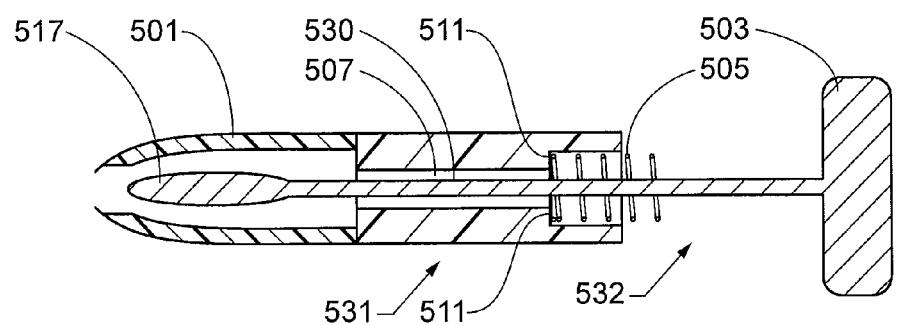
FIG. 35 is a cross-sectional side view of the spring-loaded obturator within the trocar tube.
Figure 36:
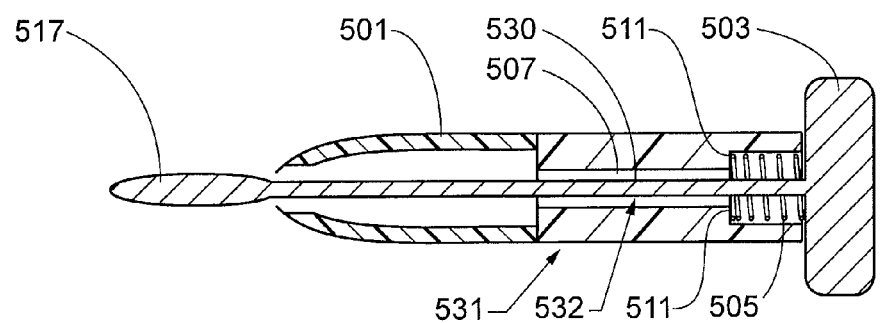
FIG. 36 is a cross-sectional side view showing the spring-loaded obturator compressed by the flanged trocar tube with the obturator tip extending distally from the dilator tip according to an embodiment of the present invention.

FIG. 34 depicts an obturator 532 with the proximal region of elongated shaft 530 having coiled springs 505. FIG. 34 also shows corresponding trocar tube 531, into which obturator 532 is inserted. Trocar tube 531 contains flanges 511 located at the proximal end. FIG. 35 shows obturator 532 fully inserted into lumen 507 of trocar tube 531. FIG. 36 shows flanges 511 at the proximal end of obturator 532 engaging coiled springs 505. As obturator handle 503 is forced distally, flanges 511 compress coiled springs 505. In addition, obturator tip 517 extends distally through longitudinal slot 504 of dilator tip 501 and eventually punctures the desired tissue, as shown in FIG. 36. The compressed spring coils 505 urge obturator 532 back into the retracted proximal position when they are not being pushed by the user. Spring coils 505 also provide stability to flexible obturator 532 such that a precise cut can be made.

The combination of a longitudinally slotted 504 dilator tip 501, corresponding to the geometry of obturator tip 517, and a coiled spring 505, wrapped around the proximal end of elongated shaft 530 of obturator 532, reinforce the blade to enhance cutting performance.

Figure 37:
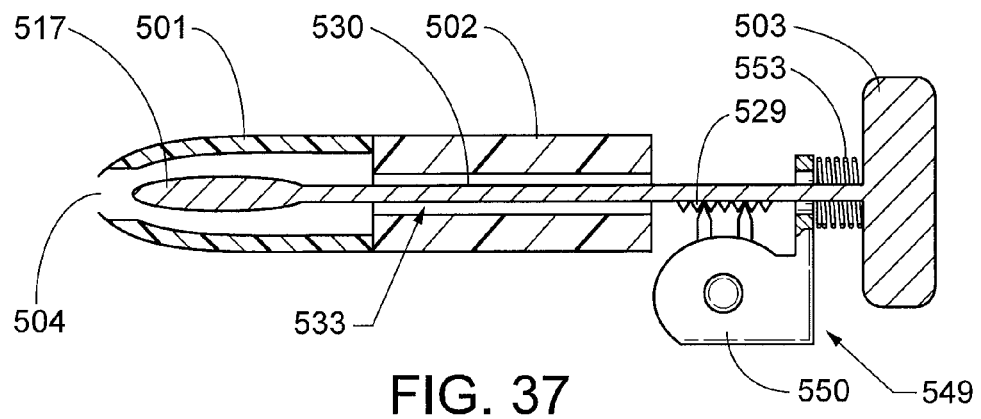
FIG. 37 is a cross-sectional side view showing a ratchet mechanism for extension and retraction of the obturator within the trocar tube according to an embodiment of the present invention.

The safety trocar may also include a ratchet mechanism 549 to extend and retract obturator tip 517. FIG. 37 shows a side view of obturator 533 with a ratchet mechanism 549. The ratchet mechanism 549 consists of a pivoting toothed cam 550, which engages matching teeth 529 on the proximal end of elongated shaft 530 of obturator 533. A spring 553 connected to the handle 503 of trocar tube 502 allows for extension of obturator tip 517 in small incremental distances through longitudinal slot 504 of dilator tip 501. Such a ratchet-like operation permits obturator 533 to incrementally extend to create the necessary tissue puncture while providing tactile feedback to the physician indicating that obturator 533 is being advanced through the tissue. The ratchet-mechanism also prevents the sudden release of back pressure associated with puncturing tissue thereby eliminating accidental extension of obturator tip 517 through tissue and organs. Other embodiments for activating obturator tip 517 to extend and retract will become apparent to one of ordinary skill in the art in view of the present disclosure. Moreover, any of the above described safety trocars can be used in the procedure for accessing a body cavity, described below.

Because protective outer sheath 506 is axially slidable relative to trocar tube 502, after obturator tip 517 has created the desired access portal 180 to the body cavity, obturator 515 and trocar tube 502 can be withdrawn from protective outer sheath 506, as shown in FIG. 38. Protective outer sheath 506 functions as an accessway to the body cavity. Because the tissue that lines stomach wall 8 is thick and tortuous, the trocar cut or puncture is typically not clean. The protective outer sheath 506 mitigates additional trauma incurred by passing the endoscope through the access port multiple times or from passing various accessories through the access port.

The above description is an exemplary application of safety trocar 500 to create an access portal to a body cavity. However, in view of the present disclosure, one of ordinary skill would know how to use the safety trocar 500 in a variety of other applications. For example, such a safety trocar can be used in colonoscopic or thoracic applications.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of accessing the peritoneal cavity for illustrative purposes only. Application of the principles of the invention to access other body cavities, such as the thoracic cavity, by way of a non-limiting example, are within the ordinary skill in the art and are intended to be encompassed within the scope of the attached claims. Moreover, in view of the present disclosure, a wide variety of safety trocars and suture exchangers will become apparent to one of ordinary skill in the art.

The invention claimed is:

1. A device for accessing a body cavity through a body wall of a patient comprising:
    a flexible, multi-lumen overtube comprising a distal end, a main lumen configured to receive an endoscope, and a plurality of outer lumens circumferentially disposed about the main lumen;
    a plurality of attachment mechanisms disposed within and deployable from the plurality of outer lumens, wherein the plurality of attachment mechanisms are configured to secure the distal end of the multi-lumen overtube against a body wall, wherein each of the plurality of attachment mechanisms comprises a suture anchor having an attached filament, the filament having a free end removably disposed within one of the plurality of outer lumens such that the free end extends proximally from a proximal end of the overtube;
    at least one pushing rod configured to be movably advanced through each of the outer lumens, the pushing rod having an elongate shaft with a distal end configured to engage and deploy the anchor of each of the plurality of suture anchors;
    a trocar comprising a tube configured to be removably inserted into the main lumen of the overtube, the trocar tube containing an elongate shaft and a cutting portion disposed on a distal end thereof, the cutting portion being configured to engage and puncture the body wall; and
    a suture exchanger configured to be removably inserted into the main lumen of the overtube, the suture exchanger comprising a shaft having an axial length larger than the axial length of the overtube, the shaft of the suture exchanger having a proximal shaft portion and a hook portion located distal to the proximal shaft portion, wherein the hook portion takes the form of a sickle having a curvature offset from a longitudinal axis of the proximal shaft portion, the curvature forming a rounded distal-most end of the suture exchanger, the hook configured to movably ensnare a portion of the filaments of each of the suture anchors when the filaments are disposed above the body wall and when the overtube is at least partially retracted away from the body wall, whereby the hook portion is configured to proximally withdraw the free end of each of the suture anchor filaments from the plurality of outer lumens and into the main lumen and towards the proximal end of the overtube, the free ends of the suture anchor filaments being extendable from the proximal end of the overtube.

2. The device of claim 1, wherein the elongate shaft and cutting portion of the trocar is an obturator comprising a wedge shaped obturator tip, and wherein the trocar tube is a sheath slidable relative to the elongate shaft and the obturator tip to selectively cover or expose the obturator tip.

3. The device of claim 1, wherein the trocar further comprises a wire guide lumen extending axially therethrough.

4. The device of claim 1 wherein the overtube comprises a plurality of longitudinal slits extending along the length of each of the plurality of outer lumens, wherein each of the slits extends towards an exterior of the overtube.

5. The device of claim 1 wherein the overtube comprises a plurality of longitudinal slits extending along the length of the main lumen, each of the slits extending between the main lumen and one of the plurality of outer lumens.

6. The device of claim 5 wherein the free ends of the filaments of the plurality of attachment mechanisms are configured to be pulled into the main lumen through one of the plurality of slits.

7. The device of claim 5, wherein when ensnared, the plurality of suture anchor filaments can be withdrawn through the longitudinal slits and into the main lumen substantially untwisted relative to each other.

8. The device of claim 1 wherein the flexible, multi-lumen overtube further comprises a valve at the proximal end to form a seal about an endoscope when an endoscope is disposed within the main lumen.

9. The device of claim 1, wherein the proximal shaft portion of the suture exchanger comprises a handle proximally extending past the proximal end of the overtube.

\* \* \* \* \*